United States Patent
Woolfe et al.

(10) Patent No.: US 6,537,582 B2
(45) Date of Patent: *Mar. 25, 2003

(54) ANTI-INFLAMMATORY PHARMACEUTICAL FORMULATIONS

(75) Inventors: Austen John Woolfe, North Weald (GB); Siobhan Greene, Waterford (IE); Gordon McIntyre, Bishop's Stortford (GB); Nitin Vadilal Sheth, Goshen, NY (US)

(73) Assignee: Norton Healthcare Ltd., Harlow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/002,411

(22) Filed: Nov. 14, 2001

(65) Prior Publication Data

US 2002/0054908 A1 May 9, 2002

Related U.S. Application Data

(63) Continuation of application No. 09/479,430, filed on Jan. 7, 2000, and a continuation-in-part of application No. 09/414,673, filed on Oct. 7, 1999, and a continuation-in-part of application No. 09/394,179, filed on Sep. 10, 1999, now abandoned.
(60) Provisional application No. 60/099,814, filed on Sep. 10, 1998.

(51) Int. Cl.⁷ .................................................. A61K 9/14
(52) U.S. Cl. ........................ 424/489; 424/475; 424/490
(58) Field of Search ................................ 424/400, 464, 424/468, 470, 451, 457, 458, 489

(56) References Cited

U.S. PATENT DOCUMENTS

| | | | |
|---|---|---|---|
| 5,232,704 A | 8/1993 | Franz et al. ................. 424/456 |
| 5,626,874 A | 5/1997 | Conte et al. ................. 424/464 |
| 5,698,225 A * | 12/1997 | Gimet et al. ................. 424/475 |
| 5,840,332 A | 11/1998 | Lerner et al. ................. 424/464 |
| 5,916,910 A | 6/1999 | Lai ............................. 514/423 |
| 5,989,463 A | 11/1999 | Tracy et al. ................. 264/4.1 |
| 6,106,862 A * | 8/2000 | Chen et al. ................. 424/468 |
| 6,183,779 B1 * | 2/2001 | Ouali et al. ................. 424/472 |
| 6,287,600 B1 * | 9/2001 | Ouali et al. ................. 424/472 |
| 6,319,519 B2 * | 11/2001 | Woolfe et al. ............... 424/472 |
| 6,387,410 B1 * | 5/2002 | Woolfe et al. ............... 424/489 |

FOREIGN PATENT DOCUMENTS

| | | | | |
|---|---|---|---|---|
| EP | 1020182 A2 * | 7/2000 | | |
| EP | 1068867 A2 * | 1/2001 | | |
| HU | 25023 | 5/1983 | | |
| JP | 63287543 | 11/1988 | | |
| WO | WO91/16886 * | 11/1991 | | |
| WO | WO/91/16895 | 11/1991 | ......... A61K/31/557 |
| WO | WO/99/12524 | 3/1999 | ............ A61K/9/20 |
| WO | WO00/01368 * | 1/2000 | | |
| WO | WO00/15200 * | 3/2000 | | |
| WO | WO00/56339 * | 9/2000 | | |
| WO | WO 01/24778 A1 | 4/2001 | | |

OTHER PUBLICATIONS

Rudnic, et al., "Oral Solid Dosage Forms", Remington's Pharmaceutical Sciences, Chapter 89, 1990, p. 1633, 1321.

* cited by examiner

Primary Examiner—Konata George
(74) Attorney, Agent, or Firm—Beyer Weaver & Thomas LLP

(57) ABSTRACT

An oral pharmaceutical dosage form including a mixture of a delay release formulation of a non-steroidal anti-inflammatory drug (NSAID) and a mixture containing a prostaglandin and one or more excipients.

19 Claims, No Drawings

ANTI-INFLAMMATORY PHARMACEUTICAL FORMULATIONS

This is a continuation application of prior application Ser. No. 09/479,430, filed Jan. 7, 2000; Continuation-in-Part of application Ser. No.: 09/414,673, filed Oct. 7, 1999; Continuation-in-Part of application Ser. No.: 09/394,179, filed Sep. 10, 1999; and Provisional Application No.: 60/099,814, filed on Sep. 10, 1998.

This invention relates to pharmaceutical formulations of anti-inflammatory drugs, particularly non-steroidal anti-inflammatory drugs (NSAIDs).

These NSAIDs are used for the treatment of inflammatory conditions such as osteoarthritis or rheumatoid arthritis. A side effect of the oral administration of NSAIDs particularly with long term usage, is a liability to ulcerogenic effects. NSAID induced ulcers in the stomach are potentially dangerous because few or no symptoms may be detected until significant damage has been caused. Certain prostaglandins, for example misoprostol have been shown to reduce and even prevent such ulcers.

Various patent applications relate to use of misoprostol with immediate release drugs, for example GB-A2135881 (Farmitalia Carlo Erba), WO91/16896 (G D Searle), or where a gastric resistant coating is put over the NSAID in an attempt to reduce further gastric erosion due to release in the stomach of the NSAID, for example WO91/16895, WO91/16886 (G D Searle).

There is an increasing use of sustained release preparations of NSAID drugs to reduce the number of doses required by the patient each day. Although the theory of such preparations is that the majority of the drug is released in the intestine rather than the stomach, in practice there is a significant occurrence of gastric problems. This may be due to release of small amounts of drug within the stomach.

The incorporation of misoprostol into such products to reduce the potential for such problems has not previously been disclosed.

According to the present invention an oral pharmaceutical dosage form includes a mixture of a delay release formulation of a NSAID and a mixture containing one or more excipients and a prostaglandin.

The delay release NSAID formulation preferably comprises coated beads or pellets.

An alternative formulation comprises coated granules.

The prostaglandin mixture may be provided in the form of a powder which is mixed with the NSAID formulation within the dosage form.

The dosage form may comprise a tablet, capsule, granule or other commonly used configuration. However preferred dosage forms comprise a capsule containing multi-particulate beads or granules of the NSAID formulation together with the powdered prostaglandin mixture. The NSAID beads or granules preferably have coatings adapted to provide programmed release according to the position in the gastrointestinal tract. Use of such coated beads or granules provides a more repeatable release along the gastrointestinal tract and may reduce gastric erosion because the small pellets or beads are easily moved and do not adhere readily to the folds of the gastric wall.

Beads or granules for use in accordance with this invention may have a single slowly erodible coat or may comprise mixtures of beads or granules with differing levels or types of coating adapted to provide a continuous or distributed release profile through the gastrointestinal tract. The delay afforded may range from a minimal delay to several hours, dependent on the pH of the gastrointestinal tract in the immediate vicinity.

The NSAID is preferably but not exclusively one of reasonably low weight per standard dose, that is 200 mg or below. Examples of suitable NSAIDs include tiaprofenic acid, piroxicam, flubiprofen, tenoxicam, meloxicam or similar molecules. Salts or other derivatives of these drugs may be employed in a conventional manner. Most preferably the drug is diclofenac sodium, ketoprofen or indomethacin. Mixtures may be used.

It is possible to produce the particles or beads by conventional means. Techniques that can be used can include coating the drug on a non-pariel core preferably composed of inert sugar or similar substance and then overcoating with the required coating before encapsulation. The following steps may be employed.

i. Preparation of inert core by conventional pan coating method ii Active coating by using rotary type fluidized bed.

iii Protective coating by using rotary type fluidized bed.

iv Enteric coating by using rotary type fluidized bed.

The procedure disclosed in EP-A-519144 may be used.

Drug delivery using capsules avoids a further compression step as may be necessary during tablet manufacture.

An alternative method is to form beads or particles by co-acervation or alternatively by precipitation from solution as described by Zaniboni, Fell and Collett, (Int.J.Pharm, 1995, 125, 151–5).

In a preferred technique the beads or particles may be formed by spheronisation, rotogranulation or a similar technique. If tablets are to be made, preferably the beads or particles should be soft enough to deform slightly under compression to avoid cracking but not too soft so as to deform significantly as deformation may also cause cracking or rupture of the coat. A mixture of drug with a suitable amount of an excipient or excipients can be found by simple experiments. Suitable excipients include polyvinyl pyrrolidone, sugars and cellulose derivatives particularly microcrystalline cellulose.

Granules, for example composed of diclofenac sodium and a methyl methacrylate (eg Eudragit L 30 D-55) may be prepared by blending the ingredients in a planetary mixer with slow addition of water to produce granules. In a preferred process very fine granules are produced to avoid a need for milling before compaction into tablets or incorporation into capsules. Use of granules with the dimension of 200–1000 μm, preferably 300 to 500 μm is particularly suitable. Tablets may be produced by coating these granules with a barrier coating material for example a cellulosic material such as hydroxypropylmethyl cellulose or hydroxypropyl cellulose. Tablets may be produced by coating these granules.

An alternative method of forming coated granules is by spraying a solution of Eudragit onto a bed of diclofenac sodium or other drug and any necessary excipients for example using a fluid bed coating apparatus. The process is preferably controlled to produce fine granules which do not require milling before incorporation into tablets or capsules.

The coating for the beads may include cellulose derivatives eg hydroxypropyl methyl cellulose, methacrylic acid and derivatives eg methyl methacrylates for example, Eudragit® (Rhom Pharm), especially Eudragrit L or S. Other standard enteric coating materials may be used for example phthalates, eg cellulose acetate phthalate or preferably hydroxypropylacetate phthalate or polyvinylacetate phthalate. Mixtures of these and other materials may be used to produce delay release coated beads. Normally the coating will include plasticisers eg polyethylene glycol, triacetin or phthalate esters.

The prostaglandin component preferably contains misoprostol optionally together with one or more inert excipients. The prostaglandin is normally provided as a 1:10 or 1:100 dilution on an inert cellulose or other binder or filler. Especially useful material for this invention is hydroxypropyl methyl cellulose. The dosage of prostaglandin may be chosen to be suitable to prevent or reduce stomach ulceration caused by the NSAID. A suitable dose of misoprostol is between 10–50 μg preferably 50–200 μg per dosage form but this may be increased or decreased depending on the NSAID used.

Preferred dosage forms comprise capsules, preferably hard gelatin capsules.

Tablets where the prostaglandin is mixed with one or more binding agents may be bi-layer tablets wherein the NSAID is formed into a first layer and the prostaglandin is then compressed onto it. A tri-layer tablet with an inert intermediate barrier layer between the NSAID and prostaglandin layers may be employed.

In preferred embodiments of the invention, the potential for gastric erosion is reduced by ensuring that the prostaglandin is released before the NSAID. Any beads for immediate or rapid release are coated with an inert coating which defer solubility in gastric fluid, for example for a period of 30 minutes. Such materials include cellulose derivatives for example hydroxypropyl methyl cellulose, methyl or ethyl celluloses or other sealants eg Zein. Thin coatings of methacrylate derivatives eg polyhydroxymethacrylate or other materials such as hardened gelatine, waxes, starches or polyvinyl pyrrolidone may be used. Other portions of the beads may be coated with methacrylate derivatives, phthalate, for example hydroxypropyl methyl cellulose phthalate or similar materials to give an appropriate release profile as is well known in the art.

The invention is further described by means of example, but not in any limitative sense.

EXAMPLE 1

Hard gelatin capsules fill was prepared containing a mixture of the following:

| | |
|---|---|
| delay release ketoprofen beads | 250 mg |
| misoprostol | 20 mg |
| (diluted 1:100 on hydroxypropylmethylcellulose) | |
| lactose (anhydrous) | 160 mg |
| hydrogenated vegetable oil | 4 mg |

The beads were prepared by spray coating a suspension or solution of ketoprofen onto a non-pareil sugarcore, together with a binder eg polyvinylpyrollidone or hydroxypropylmethyl cellulose. The beads were subsequently coated with a delay release coating eg methylmethacrylate (eg Eudragit (Trade Mark)). Mixtures of beads with various levels of coating were used to give the required therapeutic release pattern.

In a fluidized bed apparatus, uniform spherical inert sugar sphere cores were coated with a first layer consisting of the compounds, an inert water soluble polymer such as hydroxy-propylmethylcellulose or hydroxypropylcellulose, and talc. The second layer consisted of an inert water soluble polymer such as hydroxypropylmethylcellulose or hydroxypropylcellulose, talc and a pigment such as titanium dioxide. The third and enteric coating layer consisted of an enteric coating polymer such as co-polymerized methacrylic acid/methacrylic acid methyl esters, a plasticiser such as triethy acetate or similar plasticisers, and talc.

The layers were applied by conventional fluidized bed coating techniques using aqueous solutions or dispersions.

Pseudo zero release was obtained by use of a mixture of beads released at various pHs or at various times dependent on the type of coating.

The beads in Example 1 contained 40% ketoprofen giving a dose per capsule of 100 mg plus 100 μg misoprostol.

The mix was then filled into suitable hard gelatine capsules.

EXAMPLE 2

The following formulation was employed:

| | |
|---|---|
| delay release diclofenac beads | 214 mg |
| microcrystalline cellulose (dried) eg Avicel R PH112 | 150 mg |
| misoprostol (1 in 100 dilution on HPMC) | 20 mg |
| stearic acid | 4 mg |
| talc | g mg |

EXAMPLE 3

The following formulation was mixed with water in a planetary mixer to make enteric coated granules:

| | |
|---|---|
| diclofenac sodium | 96.28 |
| Eudragit L 30 D-55 | 3.8% |

The granules were dried and compacted into layered tablets having the following composition:

| | |
|---|---|
| diclofenac-containing granules | 26.0% |
| microcrystalline cellulose | 73.5% |
| magnesium stearate | 0.5% |

The tablets were compared to a proprietary diclofenac containing tablet available under the trade mark Arthrotec. Bioequivalence studies showed the properties to be essentially similar.

Beads containing 35% diclofenac sodium ie 75 mg drug per dose were prepared.

The beads were formed as previously described, or by mixing with a bulking agent eg microcrystalline cellulose, moistening with water, extruding and spheronising to give spherical or ovoid particles about 0.5 mm to 1.5 mm in diameter. These were dried and coated as previously described using a standard coating agent. The beads were mixed as required to give the required release profile.

The beads are usually provided with a coating to prevent immediate release in the stomach, particularly release before the misoprostol has dissolved.

EXAMPLE 4

A two layer tablet was made as follows:
The following ingredients were mixed together:

| | |
|---|---|
| Diclofenac sodium | 75.95% |
| Eudragit 130-d55 (30% solid dispersion) | 12.66% |
| Lactose (20 mesh) | 11.4% |
| Water | |

The mixture was blended, dried and milled to give diclofenac-containing granules. The granules (25%) were mixed with microcrystalline cellulose (Avicel pH 200 and pH 112) to give a total of 69%. Dry Eudragit l100 powder (5%) and hydrogenated castor oil (1%) were added. The mixture was pressed into half tablets with a tablet weight of 400 mg.

A misoprostol layer was formed as follows:
A misoprostol dispersion (1:100) 6.7% was combined with microcrystalline cellulose (Avicel pH 112) 88.33%, croscarmellose sodium (4%) and hydrogenated castor oil to give a tablet weight of 300 mg. The combined bi-layered tablet had a total weight of 700 mg.

Dissolution properties were determined by exposure to acid medium for two hours followed by measurement of dissolution in alkaline buffer. The following results were obtained.

| | SOLUBILITY | |
|---|---|---|
| Time in alkaline buffer | Example 4 tablets | Arthrotec tablets |
| 30 sec | 1.6–5.0 | 0–0.5 |
| 5 min | 11–13 | 1.3–3.1 |
| 30 min | 51–60 | 61–71 |
| 60 min | 86–90 | 74–96 |

What is claimed is:

1. An oral pharmaceutical dosage form, comprising a mixture of a delay release formulation of a non-steroidal anti-inflammatory drug (NSAID) and a mixture containing a prostaglandin and one or more excipients, wherein the prostaglandin mixture is a powder and the dosage form contains multi-particulate coated particles of the NSAID formulation together with the powdered prostaglandin mixture.

2. A dosage form as claimed in claim 1, wherein the NSAID formulation comprises coated beads or granules.

3. A dosage from as claimed in claim 2, wherein the NSAID formulation comprises coated granules.

4. A dosage form as claimed in claim 3, wherein the granules have a dimension of 200–1000 μm.

5. A dosage form as claimed in claim 4, wherein the granules have a dimension of 300–500 μm.

6. A dosage form as claimed in claim 1, wherein the prostaglandin is misoprostol.

7. A dosage form as claimed in claim 2, comprising a mixture of beads or granules with different levels or types of coating.

8. A dosage form as claimed in claim 1, wherein the NSAID is selected from the group consisting of tiaprofenic acid, piroxicam, flubiprofen, tenoxicam, meloxicam and salts and derivatives thereof.

9. A dosage from as claimed in claim 8, wherein the NSAID is selected from the group consisting of diclofenac sodium, ketoprofen and indomethacin and mixtures thereof.

10. A dosage form as claimed in claim 6, wherein the dosage of misoprostol is 50 to 200 μg per dosage form.

11. A dosage form as claimed in claim 1, wherein the particles comprise coatings including the drug on non-pareil cores.

12. A dosage form as claimed in claim 1, wherein the particles are made by co-acervation or precipitation from solution.

13. A dosage form as claimed in claim 11, wherein the particles are made by spheronisation or rotogranulation.

14. A dosage from as claimed in claim 11, wherein the coating includes the drug and an excipient selected from the group consisting of: polyvinyl pyrrolidone, sugars and cellulose derivatives.

15. A dosage form as claimed in claim 2, wherein the beads or granules have a coating of one or more compounds selected from the group consisting of: hydroxypropyl methyl cellulose, methacrylic acid and derivatives, methyl methacrylates, cellulose acetate phthalate, hydroxypropylacetate phthalate, polyvinylacetate phthalate and mixtures thereof.

16. A dosage form as claimed in claim 15, wherein the coating includes a plasticiser selected from the group consisting of: polyethylene glycol, triethyl acetate or phthalate esters.

17. A dosage form as claimed in claim 1 comprising a filled hard gelatin capsule.

18. A dosage form as claimed in claim 1, comprising a bi-layer or tri-layer tablet.

19. A dosage form as claimed in claim 18, wherein particles of the NSAID are coated with a coating selected from the group consisting of: hydroxypropyl methyl cellulose, methacrylic acid and derivatives, methyl methacrylates, cellulose acetate phthalate, hydroxypropylacetate phthalate, polyvinylacetate phthalate and mixtures thereof are compressed into a first layer and a second layer comprising the prostaglandin and excipients is compressed onto the first layer.

* * * * *